(12) United States Patent
Dombrowski et al.

(10) Patent No.: US 12,103,256 B2
(45) Date of Patent: Oct. 1, 2024

(54) OPTICAL TUBE BENDER

(71) Applicant: Lumitex, Inc., Strongsville, OH (US)

(72) Inventors: Joseph Dombrowski, Medina, OH (US); Nicolette Diehl, Brunswick, OH (US)

(73) Assignee: Lumitex, Inc.

( * ) Notice: Subject to any disclaimer, the term of this patent is extended or adjusted under 35 U.S.C. 154(b) by 197 days.

(21) Appl. No.: 17/396,970

(22) Filed: Aug. 9, 2021

(65) Prior Publication Data

US 2022/0048262 A1 Feb. 17, 2022

Related U.S. Application Data (60) Provisional application No. 63/066,444, filed on Aug. 17, 2020.

(51) Int. Cl.
| | |
|---|---|
| *F21V 8/00* | (2006.01) |
| *A61B 90/30* | (2016.01) |
| *B29C 53/08* | (2006.01) |
| *B29D 11/00* | (2006.01) |

(52) U.S. Cl.
CPC ........ *B29D 11/00663* (2013.01); *A61B 90/30* (2016.02); *B29C 53/083* (2013.01); *G02B 6/0005* (2013.01); *A61B 2090/306* (2016.02)

(58) Field of Classification Search
CPC .............. B29D 11/00663; A61B 90/30; A61B 2090/306; B29C 53/083; G02B 6/005; G02B 6/00; G02B 27/0994; G02B 6/0028
See application file for complete search history.

(56) References Cited

U.S. PATENT DOCUMENTS

| | | | | |
|---|---|---|---|---|
| 4,173,393 | A * | 11/1979 | Maurer | C03B 37/027 |
| | | | | 385/128 |
| 4,605,990 | A * | 8/1986 | Wilder | A61B 90/30 |
| | | | | 600/245 |
| 5,951,544 | A * | 9/1999 | Konwitz | A61B 18/22 |
| | | | | 606/17 |
| 2005/0171408 | A1* | 8/2005 | Parker | A61B 17/0293 |
| | | | | 600/249 |
| 2006/0189845 | A1* | 8/2006 | Maahs | A61B 1/0051 |
| | | | | 600/146 |
| 2009/0024190 | A1* | 1/2009 | Irvine | A61B 18/24 |
| | | | | 607/89 |
| 2015/0196196 | A1* | 7/2015 | Vayser | A61B 17/0218 |
| | | | | 600/245 |
| 2019/0290888 | A1* | 9/2019 | Rochon | A61B 18/245 |
| 2019/0350670 | A1* | 11/2019 | Grey | A61B 17/02 |

* cited by examiner

*Primary Examiner* — Yingchuan Zhang
*Assistant Examiner* — Sebastian X Lukjan
(74) *Attorney, Agent, or Firm* — Renner, Otto, Boisselle & Sklar, LLP (57) ABSTRACT

A light guide bender (also referred to as an optical tube bender) is provided including an integrated bending mechanism that allows the surgical tube to be bent to the appropriate length (e.g., matching the retractor height). By bending the tube at an angle, potential obstruction caused by the optical fiber is reduced and the need to create various lengths of optical tubing is also eliminated. In one embodiment, the surgical tube may also include markings designating length of the surgical tube. For example, if 200 mm of surgical tubing is needed, then the marking for 200 mm can be located on the surgical tubing and the tubing can be bent at this location.

11 Claims, 7 Drawing Sheets

OPTICAL TUBE BENDER

RELATED APPLICATIONS

This application claims the benefit of 63/066,444 filed on Aug. 17, 2020. Which is herein incorporated by reference in its entirety.

TECHNICAL FIELD

The present disclosure relates generally to surgical instruments and more particularly to an illumination system for surgical instruments.

BACKGROUND

To improve illumination in operating rooms, illuminating devices may be attached to surgical instruments (e.g., to illuminate a surgical cavity). For example, surgical retractors may include surgical tubing (also referred to as optical fiber or light guide) attached to the surface of the light guide and positioned to shine into the surgical cavity.

SUMMARY

Current illuminating systems applied to surgical instruments do not provide surgical tubing having custom lengths to accommodate various retractor heights. For example, different surgeries require different lengths of surgical tubing to illuminate a surgical area. To accommodate these different needs, either multiple different lengths of surgical tubing need to be available and selected by a surgeon or a longer length of surgical tubing is used and any excess tubing needs to be accounted for outside of the surgical cavity. The presence of excess surgical tubing is a problem because the unused surgical tubing may obstruct access to the surgical site.

The present disclosure provides a light guide bender (also referred to as an optical tube bender) including an integrated bending mechanism that allows the surgical tube to be bent to the appropriate length (e.g., matching the retractor height). By bending the tube at an angle, potential obstruction caused by the optical fiber is reduced and the need to create various lengths of optical tubing is also eliminated. In one embodiment, the surgical tube may also include markings designating length of the surgical tube. For example, if 200 mm of surgical tubing is needed, then the marking for 200 mm can be located on the surgical tubing and the tubing can be bent at this location.

The present disclosure provides a light guide bender including a framework for shaping a contacting portion of the light guide when a force is applied to the light guide.

The present disclosure also provides an optical tube arranging apparatus including the light guide bender and a clip configured to engage with a medical instrument and to maintain a position of the light guide relative to the medical instrument.

The present disclosure further provides an illuminating system including the optical tube arranging apparatus and a light guide having markings indicating a length of the optical tube.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

The present invention is described below in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

DETAILED DESCRIPTION

According to a general embodiment, a light guide bender is provided for reshaping a light guide. The bender has a contoured receiving surface for receiving the light guide, such that when a force is applied to the light guide, a contacting portion of the light guide presses against the receiving surface and the light guide is bent based on the contour of the receiving surface.

Figure 1:
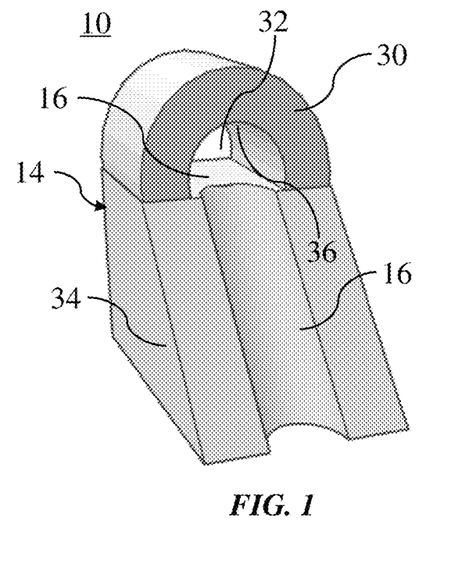
FIG. 1 is a front perspective of an exemplary embodiment of a light guide bender.
Figure 2:
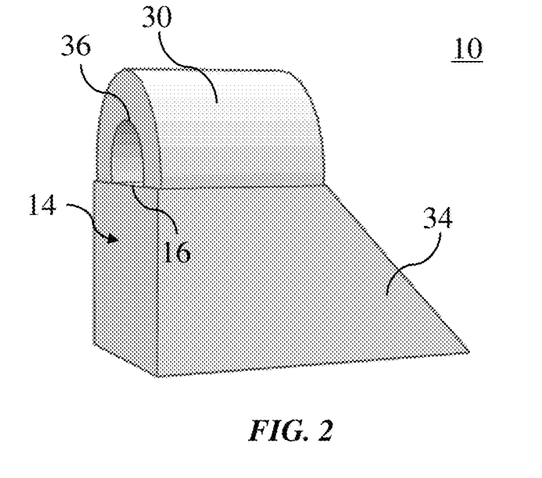
FIG. 2 is a side perspective of the light guide bender of FIG. 1.

Turning to FIGS. 1 and 2, an exemplary embodiment of a light guide bender 10 for reshaping a light guide 12 is shown. The light guide bender 10 includes a framework 14 having a contoured receiving surface 16. The receiving surface 16 is configured to receive the light guide 12, such that a contacting portion 18 of the light guide 12 is supported by the receiving surface 16 with a proximal portion 20 and a distal portion 22 of the light guide 12 extending away from the framework 14. The receiving surface 16 is shaped, such that when a force 21 is applied to the light guide 12 the contacting portion 18 presses against the receiving surface 16 and a contoured portion 26 of the light guide 12 is generated from a part of the proximal portion 20 of the light guide 12 being bent based on the contour of the receiving surface 16.

In the embodiment shown in FIGS. 1-5, the framework 14 includes a housing 30 having a channel 32 and a projection 34. The projection 34 includes at least a portion of the receiving surface 16. The channel 32 may be shaped to receive the light guide 12, such that the proximal portion 20 and the distal portion 22 of the light guide 12 extend away from the framework 14. The channel 32 includes a pressing surface 36 opposite the receiving surface 16. The projection 34 may be mechanically attached to the housing 30, such that when the force 21 is applied to the light guide 12 (such that the contacting portion 18 presses against the receiving surface 16), a cantilevered portion 38 of the light guide 12 presses against the pressing surface 34 of the housing 30. The cantilevered portion 38 of the light guide 12 may be distal to the contacting portion 18 of the light guide 12.

Figure 6:
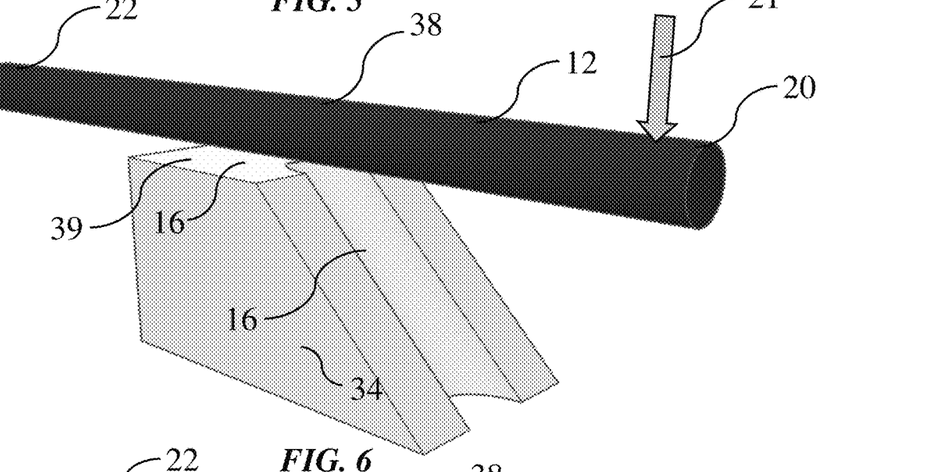
FIG. 6 is a front perspective view of an exemplary embodiment of a light guide bender and a straight light guide.
Figure 7:
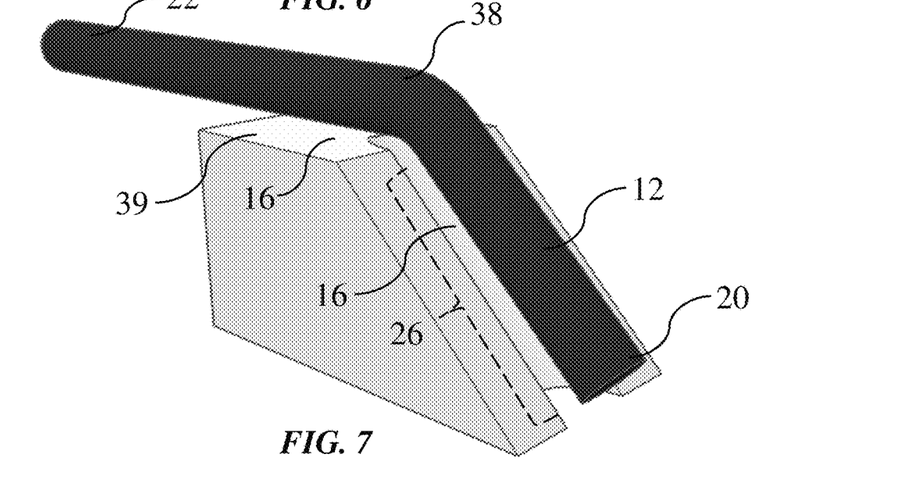
FIG. 7 is a front perspective view of the light guide bender of FIG. 6 after the light guide has been bent using the light guide bender.

As shown in the embodiments depicted in FIGS. 6 and 7, the framework 14 may include the channel 32 and the projection 34, without the housing 30. Using this embodiment, a user may place another object (such as a clamp or their hand) on a pushing surface 39 (e.g., the top) of the framework 14 when applying force 21 to the light guide at a location proximal on the light guide relative to the pushing surface 39 of the framework 14.

The framework 14 may be made of any suitable material sufficiently rigid for the light guide 12 to be bent towards the framework 14 when a force 21 is applied to the guide 12. For example, the framework 14 may be made of metal and/or ceramic. The receiving surface 16 of the framework 14 may include grooved and/or non-grooved surface as shown in the figures. For example, at least a portion of the receiving surface 16 may include a depression configured to receive a portion of the light guide 12. The receiving surface 16 may also have any suitable contour. For example, the contour may be less than, greater than, or approximately equal to (e.g., within five degrees of) ninety degrees (90°).

Figure 8:
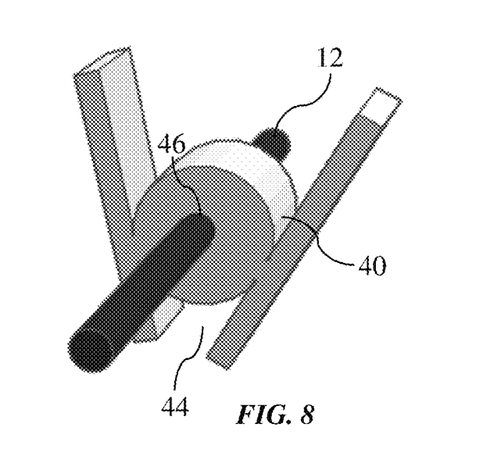
FIG. 8 is a front perspective view of an exemplary embodiment of a clip and a light guide.
Figure 9:
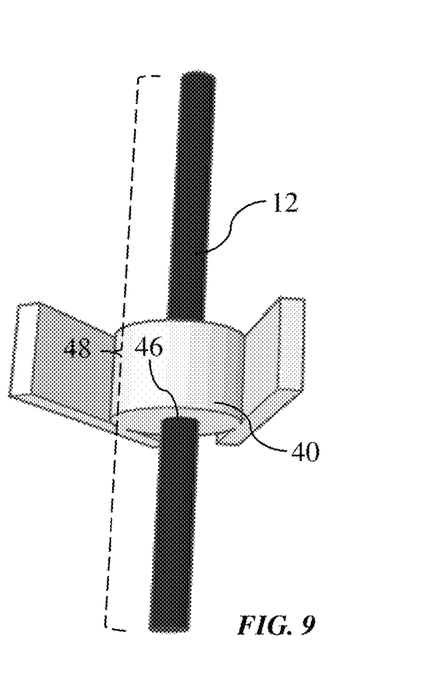
FIG. 9 is a top perspective view of the clip and light guide of FIG. 8.
Figure 10:
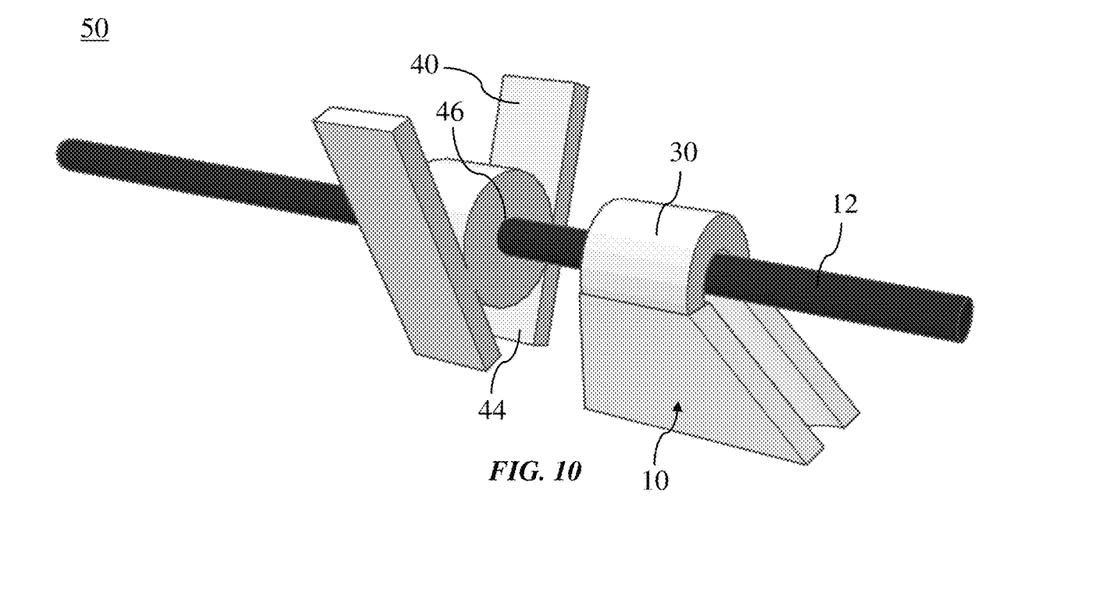
FIG. 10 is a perspective view of an exemplary embodiment of an illuminating system including a light guide and an optical tube arranging apparatus including a clip and a light guide bender.
Figures 11, 12, 13, 14:
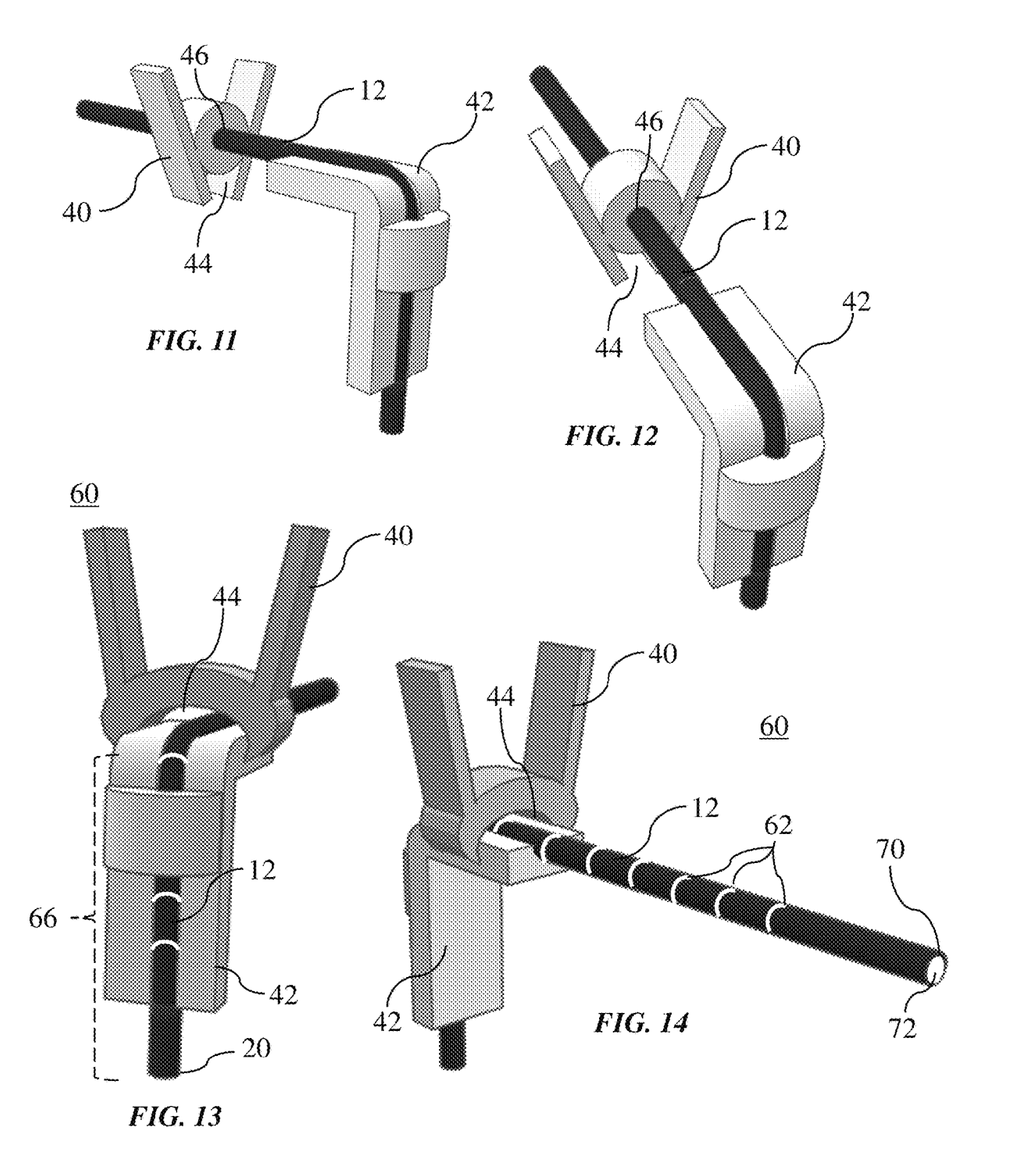
FIG. 11 is a side perspective view of an exemplary embodiment of a clip, light guide, and a medical instrument.
FIG. 12 is a top perspective view of the clip, light guide, and medical instrument of FIG. 11.
FIG. 13 is a front perspective view of an exemplary embodiment of a clip attached to a medical instrument and maintaining the position of a light guide.
FIG. 14 is a side perspective view of the clip, light guide, and medical instrument of FIG. 13.

In the exemplary embodiment shown in FIGS. 8-10, a clip 40 has been positioned along the length of the light guide 12. The clip 40 may be positionable between an open state and a closed state. As shown in FIG. 10, the clip 40 may be positioned along the length for the light guide 12 before the light guide is bent using the light guide bender. In FIGS. 11 and 12, the bent light guide 12 including the clip 40 have been positioned adjacent to a medical instrument 42, but the clip 40 has not engaged with the medical instrument.

In the exemplary embodiment shown in FIGS. 13 and 14, the clip 40 is shown in the closed state. In the closed state, the clip 40 is configured to engage with a medical instrument 42 to form an enclosed area 44 bounded by the clip 40 and the medical instrument 42. In this way, the clip 40 may be used to maintain the position of the light guide 12 relative to the medical instrument 42.

Figure 15:
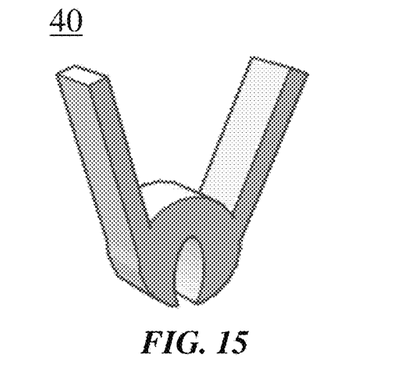
FIG. 15 is an exemplary embodiment of a clip.

In the open state, the clip 40 is configured to be positionable relative to the medical instrument 42 and the light guide 12 such that, when the clip 40 is transitioned between the open state and the closed state, the clip 40 engages with the medical instrument 42 to form the enclosed area 44 (i.e., such that a portion of the light guide 12 is retained within the enclosed area 44). For example, as shown in FIG. 15, the clip 40 may be biased (e.g., via a spring) to transition towards the closed state at rest (i.e., when a force is not being applied to the clip 40). A force may be applied to the clip 40 to open the clip 40 (i.e., maintain or transition the clip 40 towards the open state) so that the clip 40 may be placed adjacent to the medical instrument 42, such that when the force is removed from the clip 40 the clip 40 closes (i.e., transitions to the closed state) and engages (e.g., grabs) the medical instrument 42.

Returning to FIGS. 8-14, the enclosed area 44 of the clip 40 may include an enclosed passage 46 shaped to receive the light guide 12. The enclosed passage 46 may enable the clip 40 to be slidable along a length 48 of the light guide 12 and to maintain a position of the clip 40 relative to the light guide 12.

An embodiment of an optical tube arranging apparatus 50 for engaging with a medical instrument and for reshaping a light guide is shown in FIG. 10. The optical tube arranging apparatus 50 may include the light guide bender 10 and the clip 40.

Figure 16:
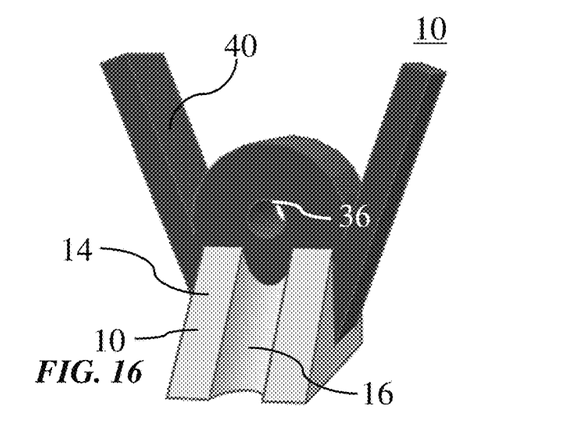
FIG. 16 is a front perspective view of an exemplary embodiment of a light guide bender removably attached to a clip.
Figure 17:
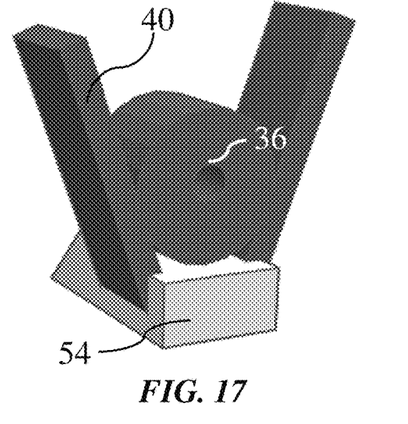
FIG. 17 is a rear perspective view of the light guide bender and removably attached clip of FIG. 16.
Figure 18:
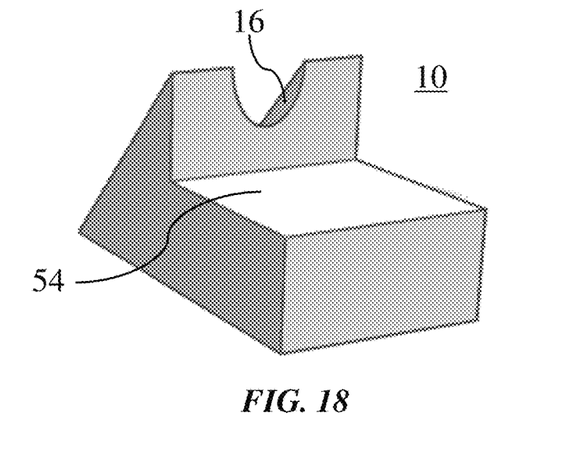
FIG. 18 is a rear perspective view of the light guide bender of FIGS. 16 and 17 without the clip.

In the embodiment shown in FIGS. 16-18, the clip 40 is separately movable from the light guide bender 10. The clip 40 is configured to releasably attach to the light guide bender 10. For example, the clip 40 may attach relative to the receiving surface 16 of the framework 14, such that the pressing surface 36 is a surface of the clip 40. In the depicted embodiment, the clip 40 attaches to a projection 54

Figure 19:
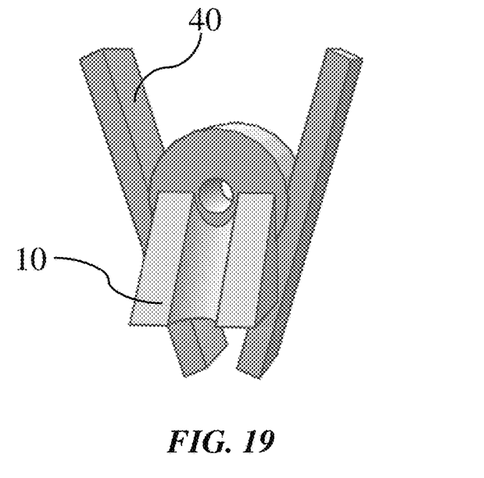
FIG. 19 is a front perspective view of a unitary light guide bender and clip.
Figure 20:
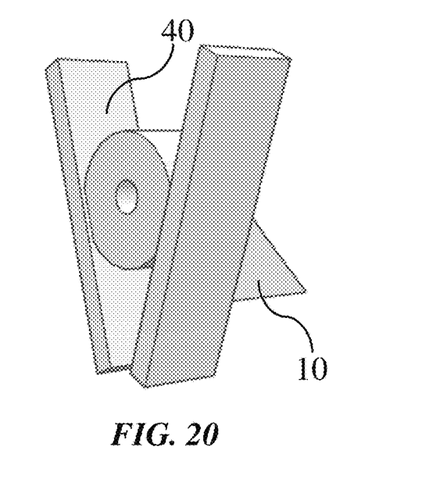
FIG. 20 is a rear perspective view of the unitary light guide bender and clip of FIG. 19.

In the embodiment shown in FIGS. 19 and 20, the clip 40 and the light guide bender 10 are mechanically connected to form a unitary body. For example, the clip 40 and light guide bender 10 may be collectively formed as a single piece. As another example, the clip 40 and the light guide bender 10 may be separately formed and permanently attached to one another (e.g., via glue, welding, etc.). In this embodiment, the clip 40 may be configured to engage with the medical instrument 42 (e.g., such that the receiving surface 16 aligns with a channel 55 of the medical instrument).

Figure 3:
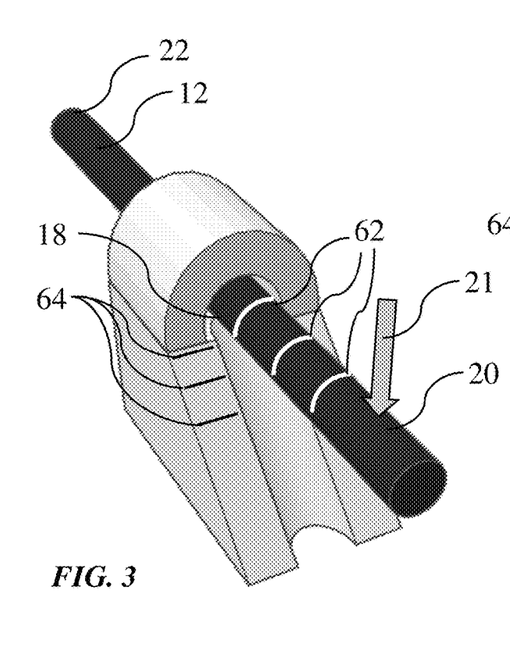
FIG. 3 is a front perspective view of the light guide bender of FIG. 1 including length markings and a straight light guide.
Figure 4:
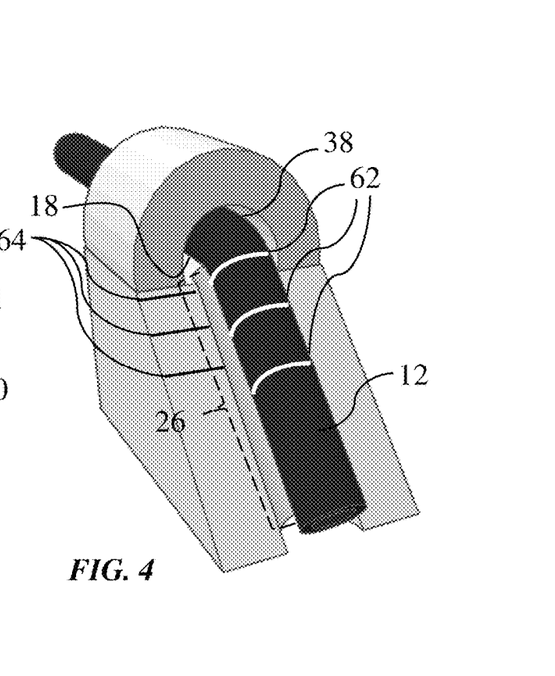
FIG. 4 is a front perspective view of the light guide bender and light guide of FIG. 3 after the light guide was bent using the light guide bender.
Figure 5:
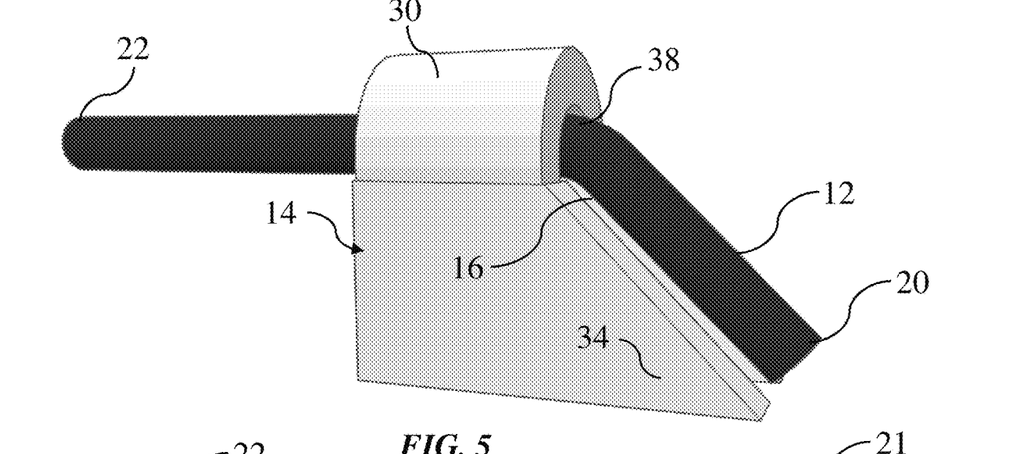
FIG. 5 is a side perspective view of the light guide bender and light guide of FIG. 4 without length markings.

In the embodiment shown in FIGS. 13 and 14, an illuminating system 60 is shown. The illuminating system 60 includes a light guide 12 having markings 62 and the optical tube arranging apparatus 50. Each of the markings 62 may indicate a distance 66 of the marking 62 from the proximal end 20 of the light guide 12. As shown in FIGS. 3 and 4, the light guide bender 12 may include scoring 64 for aligning with the markings 62 of the light guide 12 when bending the light guide 12. When the scoring 64 is aligned with the marking 62 showing the desired length from the proximal end 20, the light guide 12 may be fixed in place and force 21 may be applied to the light guide 12 to generate the contoured portion 26 of the light guide 12.

The light guide may be any suitable malleable structure for transporting light (e.g., via total internal reflection). For example, the light guide 12 may include an outer shell 70 and an optic core 72 configured to transmit light. In one embodiment, the outer shell 70 is metallic (e.g., steel or aluminum) and/or the optic core 72 includes fiber optics. In another embodiment, the outer shell 70 may be a plastic tube having a memory. The optic core 72 may have a loss of light being transmitted within the optic core 72 of less than 95%, 90%, 80%, or 75%.

The light guide 12 may have any suitable cross section that allows for the light guide 12 to interact with the medical instrument 42. For example, the medical instrument 42 may have a channel 55 for receiving the light guide 12 and the light guide 12 may be shaped to at least partially be received into the channel 55. In one embodiment, the light guide 12 has a cross section that is circular or rectangular.

The light guide 12 may have any suitable length. For example, the light guide 12 may have a length of 70 mm or 120 mm.

The medical instrument 42 may be a retractor (e.g., a surgical spinal retractor), a suction tube, or any suitable instrument.

Figure 21:
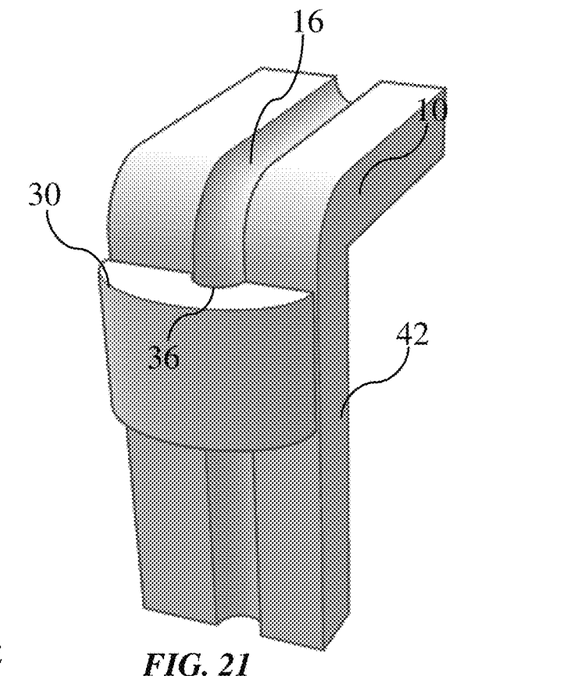
FIG. 21 is an exemplary embodiment of a light guide bender comprising a medical instrument.
Figure 22:
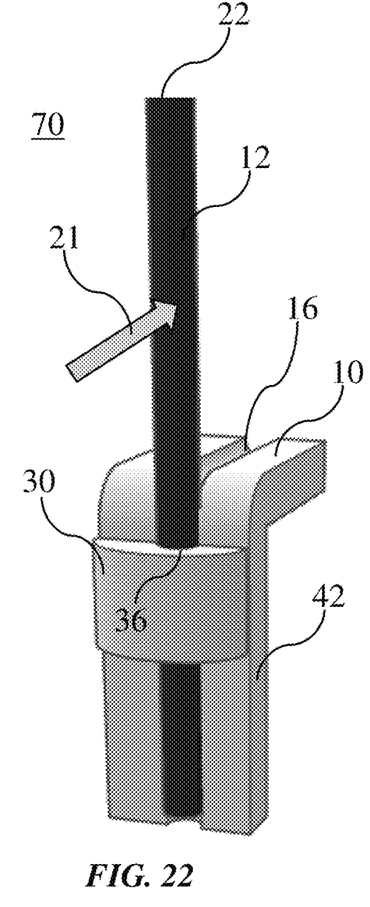
FIG. 22 is a perspective view of the light guide bender of FIG. 17 and a straight light guide.
Figure 23:
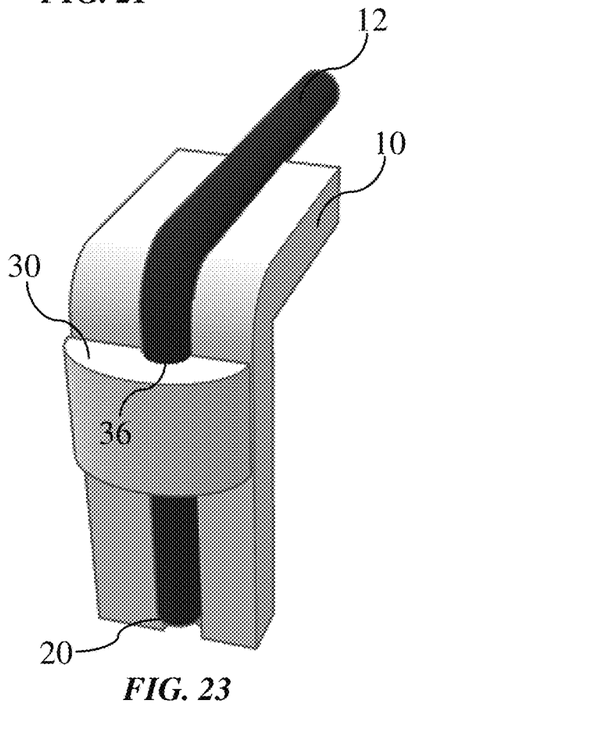
FIG. 23 is a perspective view of the light guide bender of FIG. 17 after the light guide has been bent using the light guide bender.

In the embodiment shown in FIGS. 21-23, the light guide bender 12 includes the medical instrument 42. For example, in FIG. 21 a retractor 42 acts as the light guide bender. As shown in FIG. 22, the light guide 12 may be inserted into the retractor 42 and force 21 may be applied to the light guide 12 to bend the light guide as shown in FIG. 23. In this embodiment, the housing 30 may act to maintain the position of the light guide 12 relative to the medical instrument 42, such that a clip 40 is not needed. However, in an alternative embodiment, a clip 40 may be included to improve the attachment of the light guide 12 to the medical instrument 42. In another embodiment, the medical instrument may not include a housing 30, but a clip 40 may be attached to the medical instrument, such that the clip 40 includes the pressing surface 36 as shown in FIG. 16.

In one embodiment, an illuminated medical implement 70 includes the medical instrument 42 and the illuminating system 60.

Figure 24:
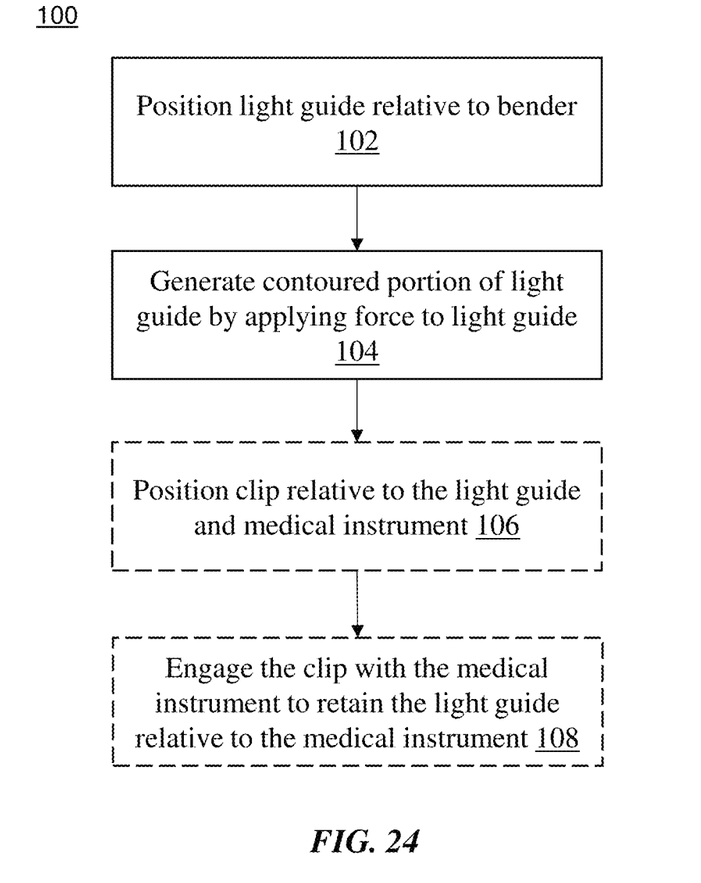
FIG. 24 is a flow diagram of an exemplary method for shaping a light guide using a light guide bender.

In the embodiment shown in FIG. 24, a method 100 for shaping a light guide 12 using a light guide bender 10 is shown. In step 102, the light guide 12 is positioned relative to the light guide bender 12, such that a contacting portion 18 of the light guide 12 is supported by a receiving surface 16 of the light guide bender 12 and such that a proximal portion 20 and a distal portion 22 of the light guide 12 extends away from the light guide bender 10.

In step 104, a contoured portion 26 of the light guide 12 is generated from a part of the proximal portion 20 of the light guide 12 by applying a force 21 to the light guide 12. The force 21 is applied such that the contacting portion 18 of the light guide 12 presses against the receiving surface 16 of the light guide bender 12 and is bent based on the contour of the receiving surface 16. For example, the portion of the light guide 12 in contact with the light guide bender 10 stays in place while the portion of the light guide 12 extending above the receiving surface 16 is bent towards the receiving surface 16 by the force applied to the light guide 12.

In optional step 108, a clip 40 is positioned relative to the light guide 12 and a medical instrument 42. In optional step 110, the clip 40 is transitioned from an open state to a closed state, such that the clip 40 engages with the medical instrument 42 to form an enclosed area 44 bounded by the clip 40 and the medical instrument 42. The clip 40 engages with the medical instrument 42 such that a portion of the light guide 12 is retained within the enclosed area 44.

In an optional step, the light guide 12 may be positioned relative to the light guide 12 bender, such that a marking 62 on the light guide 12 indicating a desired length is adjacent to the light guide bender 12.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. An illuminating system for a medical instrument comprising:
   a pliable light guide configured to maintains its shape until a user applies an active force against the light guide; and
   a light guide bender for reshaping the light guide comprising a framework having a top receiving surface and an angled receiving surface descending from a plane of the top receiving surface, wherein the top receiving surface and the angled receiving surface are configured to receive the light guide and are so dimensioned that:
      a contacting portion of the light guide is supported by the top receiving surface with a proximal portion and a distal portion of the light guide extending away from and not contacting the angled received surface of the framework; and
      when the active force is applied to the light guide by the user such that the contacting portion of the light guide presses against the top receiving surface, a contoured portion of the light guide is generated from a part of the proximal portion of the light guide being bent towards the angled receiving surface;

wherein the framework further includes a housing having a channel and a projection;
wherein the projection includes the top receiving surface;
wherein the channel is shaped to receive the light guide, such that the proximal portion and distal portion of the light guide extend away from the framework;
wherein the channel includes a pressing surface opposite the top receiving surface;
wherein the projection is mechanically attached to the housing, such that when the force is applied to the light guide such that the contacting portion presses against the top receiver a surface;
a cantilevered portion of the light guide presses against the pressing surface of the housing;
wherein the cantilevered portion of the light guide is distal to the contacting portion of the light guide.

2. The illuminating system of claim 1, wherein the light guide has a proximal end, a distal end, a length extending between the proximal end and the distal end, and markings, wherein each of the markings indicates a distance of the marking from the proximal end.

3. The system of claim 1, wherein the light guide includes an outer shell and an optic core configured to transmit light.

4. The system of claim 3, wherein the outer shell is metallic.

5. The system of claim 3, wherein the optic core includes fiber optics.

6. An illuminated medical implement comprising a medical instrument and the illuminating system of claim 1.

7. The implement of claim 6, wherein the medical instrument includes at least one of a retractor or a suction tube.

8. The implement of claim 6, wherein the medical instrument includes a channel shaped to at least partially receive the light guide.

9. An optical tube arranging apparatus for engaging with a medical instrument and for reshaping a light guide, the optical tube arranging apparatus comprising:
a pliable light guide configured to maintain its shape until a user applies an active force against the light guide; and
a light guide bender for reshaping the light guide comprising a framework having a top receiving surface and an angled receiving surface descending from a plane of the top receiving surface, wherein the top receiving surface and the angled receiving surface are configured to receive the light guide and are so dimensioned that:
a contacting portion of the light guide is supported by the top receiving surface with a proximal portion and a distal portion of the light guide extending away from and not contacting the angled receiving surface of the framework; and
when the active force is applied to the light guide by the user such that the contacting portion of the light guide presses against the top receiving surface, a contoured portion of the light guide is generated from a part of the proximal portion of the light guide being bent towards the angled receiving surface;
a clip positionable between an open state and a closed state, wherein:
in the closed state, the clip is configured to engage with a medical instrument to form an enclosed area bounded by the clip and the medical instrument;
in the open state, the clip is configured to be positioned relative to the medical instrument and the light guide such that:
when the clip is transitioned between the open state and the closed state, the clip engages with the medical instrument to form the enclosed area such that a portion of the light guide is retained within the enclosed area; and
the enclosed area of the clip includes an enclosed passage shaped to:
receive the light guide;
be slidable along a length of the light guide, and
maintain a position of the clip relative to the light guide.

10. The apparatus of claim 9, wherein the clip and the bender are mechanically connected to form a unitary body.

11. The apparatus of claim 9, wherein the clip is separately movable from the bender.

* * * * *